United States Patent [19]
Zalsman et al.

[11] Patent Number: 5,374,664
[45] Date of Patent: Dec. 20, 1994

[54] DENTAL ADHESIVES AND RESTORATION COMPOSITIONS

[75] Inventors: Baruch Zalsman, Givat-Savion; Hanna Dodiuk, Haifa; Irena Eppelbaum, Haifa; Alexander Valdman, Haifa, all of Israel

[73] Assignee: B.J.M. Laboratories Ltd., Israel

[21] Appl. No.: 65,749

[22] Filed: May 21, 1993

[30] Foreign Application Priority Data

Jun. 21, 1992 [IL] Israel .................................. 102274

[51] Int. Cl.$^5$ .......................... C08K 5/00; C08K 3/18; C08F 34/02
[52] U.S. Cl. ..................... 523/118; 524/176; 524/178; 524/398; 524/399; 524/435; 524/431; 526/271; 526/318.1
[58] Field of Search ................ 523/118, 115; 524/439, 524/430, 431, 176, 178, 398, 399, 435; 526/271, 318.1, 318

[56] References Cited

U.S. PATENT DOCUMENTS

| | | | |
|---|---|---|---|
| 4,148,988 | 4/1979 | Masuhara et al. | 526/318 |
| 4,362,842 | 12/1982 | Masuhara et al. | 524/854 |
| 4,918,136 | 4/1990 | Kawaguchi et al. | 524/751 |

FOREIGN PATENT DOCUMENTS 47-19409 of 1972 Japan .
85/00514 2/1985 WIPO .

OTHER PUBLICATIONS

Journal of Biomedical Materials Research, vol. 24, No. 8, Aug. 8, 1990, pp. 1091–1103 by Suzuky et al.
Journal of Biomedical Materials Research, vol. 23, No. 12, Dec. 12, 1989, pp. 1475–1487 by Isihara et al.

Primary Examiner—Paul R. Michl
Assistant Examiner—LaVonda R. DeWitt
Attorney, Agent, or Firm—Morgan & Finnegan

[57] ABSTRACT

Novel dental polymeric compositions useful as an adhesive dental restoration material are described. The compositions are based on a polymer obtained by the reaction of methacryloxyethyl trimellitic acid anhydride and methyl methacrylate monomer, in the presence of a free radical catalyst, being characterized by the fact that they contain at least one compound selected from the group consisting of silver, nickel, tin, silicium, copper and titanium or their oxides. The preferred amount of these compounds is in the range of between 2% and 20% by volume of the polymer. The compounds should be finely ground, possessing a particle size in the range of between 5 to 50 microns. Optionally, the compositions will contain a material capable to release anions, most preferred being fluoride-based material, in an amount of between 1% to 10% by weight of the composition. The compositions were found to impart bonding to fresh or old amalgam, as well as to dentin, enamel, porcelain and various alloys.

9 Claims, 5 Drawing Sheets

DENTAL ADHESIVES AND RESTORATION COMPOSITIONS

The present invention relates to compositions to be used for dental work. More particularly, the invention relates to compositions useful in the process of adhesive dental restoration, as well as to adhesive compositions to be used for dental work.

BACKGROUND OF THE INVENTION

The chemical or physical processes of teeth restoration in general as well as adhesive compositions for the dental art in particular, are still under investigation and therefore the technology tends to be experimental and only partially theoretical.

The strength of a joint bonded by an adhesive depends on adhesion of a composition to the surfaces joined as well as to the cohesion within the adhesive itself. The respective adhesive must cover the surfaces thoroughly and form a continuous bond line.

Conventional adhesive compositions used for dental purposes, are generally based on acrylic resins, such as acrylic or methacrylic, which in the presence of a free-radical initiator are mainly used as curable compositions for this purpose. Typical examples of such resins are based on methyl methacrylate, 2,2-bis(p-2'-hydroxy-3-methacryloxypropoxyphenyl)propane, etc.

According to Japanese Patent Number 72'19409, it is suggested to use (methacryloxy)ethyl trimellitate-ethylene glycol monomethacrylate polymer as an adhesive possessing a heat resistant anaerobic property, using benzoquinone as an inhibitor.

A successful dental composition, which is now widely used is 4-methacryloxy-methyltrimellitic anhydride known also under the name of 4-META. Thus, according to the U.S. Pat. No. 4,148,988, the dental adhesive composition is based on the following constituents:

(1) 4-META; (2) at least one ethylenically unsaturated monomer, other than 4-META, which is copolymerizable with 4-META, and (3) at least one catalyst selected from initiators and photosensitizers. It is claimed that these compositions possess a strong adhesiveness to either enamel or dentin of teeth, the resulting bonded structure being prominently excellent in its properties, such as water resistance and durability, without requiring any prior treatment. Nothing is mentioned in the patent in respect to tooth restoration.

There are many papers which deal with the physical properties of resins and cements based on 4-META. In a paper by Suzuky et al (Journal of Biomedical Materials Research 24, Aug. 8, 1990, 1091–1103) it is reported on the adhesive bonding of composite resins to dentin.

In another paper by Ishihara et al (Journal of Biomedical Materials Research, Vol. 23, No. 12, Dec. 12, 1989, 1475–1487) a new bone cement is described. It consists of 4-META and methyl methacrylate as monomers and tri-n-butyl borane as an initiator. It is mentioned that the tensile bond strength between bone and metals adhered with the cement was above 7 MPa.

According to the PCT patent application No. 85/00514, an improved method and compositions are described for the adhesion of composites to dentin, enamel and other substrates. According to the method, the substrate is first treated with an aqueous solution which comprises: at least one acidic salt of a polyvalent cation, such as titanium, vanadium, nickel, iron, copper, which can bind to dentin or enamel surface sites, at least one anion which forms a relatively water-insoluble precipitate with calcium and at least one carboxyl group. The resultant surface is further treated with a solvent containing a composition which comprises N-phenylglycine and finally treated with a solution which contains an additional compound, among others 4-META being mentioned: It is claimed that the method imparts an improved treatment of cervical erosions, root caries and other dental conditions, thus eliminating much mechanical cutting of dentin, required for retention of restorations.

It appears that all the above mentioned adhesive compositions are useful to bind dentine to a restorative material. However, the above conventional compositions do not possess sufficient bonding force to bind composite resin on top of an amalgam in restoration. Furthermore, in the use of amalgam which is commonly used in the restoration practice together with a known adhesive composition, the strength developed is poor. This might be one of the reasons why no methods are known on their use as an adhesive reagent to bind and cover amalgam restoration.

It is an object of the present invention to provide new dental compositions useful in the process of restoring teeth. It is another object of the present invention to provide new dental compositions useful for the restoration of teeth, which possess a strong adhesiveness to "fresh" (i.e. just prepared) and "old" amalgam as well as to dentin. It is a further object of the present invention to provide new dental adhesive compositions useful for the restoration of teeth, which possess a water resistance and durability. It is yet another object of the present invention to provide new dental polymeric compositions, useful for the restoration of teeth, which are polymerized in-situ.

BRIEF DESCRIPTION OF THE INVENTION

The invention relates to new dental compositions useful for the restoration of teeth which comprise a polymer produced from a methacryloxyethyl trimellitic acid anhydride (4-META) and methyl methacrylate monomer in the presence of a catalyst, optional with the addition of an inhibitor, being characterized that in said compositions is incorporated at least one compound selected from the group consisting of: silver, nickel, tin, copper, sodium, aluminium, calcium, silicium and titanium, or their oxides, in an amount of between 1% to 10% by volume of the polymer, optional in the presence of a material which is capable to release anions. The dental composition can be applied as an intermediate bonding layer or as the filling material itself.

According to a preferred embodiment, at least two of the above compounds are incorporated in an amount of between 2% to 20% by volume of the polymeric composition. The compound added should be in the form of fine particles generally having a size between 5 to 50 microns. In particular, the preferred compounds are selected from: Ag, Sn, Ti and Cu or any mixture or alloy thereof. A particular characteristic of the composition, is the fact that it is useful as a bonding material to a composite as well as a restorative material itself.

DETAILED DESCRIPTION OF THE INVENTION

The present invention provides a material to be used for teeth restoration, as adhesive composition to amalgam, as well as dentin or enamel, possessing outstanding strength which is much superior to that known from the prior art. It was found that the compound to be added in the composition selected from silver, nickel, tin, copper, sodium, aluminium, and calcium, in their metallic or oxide form, and silicium or silica, should be added in the form of fine particles. The use of such compounds in the form of an aqueous solution, did not improve at all the adhesive tensile strength as can be noticed from the comparative Examples, presented after the Examples.

According to a preferred embodiment, a material suitable to release anions, generally used in the dentistry field, is also incorporated. The amount of this material is in the range of 1% to 10% by volume of the polymeric composition. This material should contain fluoride ions which are most desirable in this field due to their beneficial effect which they impart to teeth. A typical composition of such material should contain one or more of the following constituents: calcium fluoride, aluminium fluoride, sodium fluoride, aluminum oxide, aluminum phosphate and silica.

The dental compositions according to the present invention are most useful in the restoration of teeth, providing the teeth themselves and at the same time can be successfully used as valuable dental adhesive materials for procedures such as: orthodontic purposes, repair of broken porcelain with composite resin, as adhesives for veneering a crown, bonding of amalgam to tooth structure, material for core build-up, etc.

Figure 1:
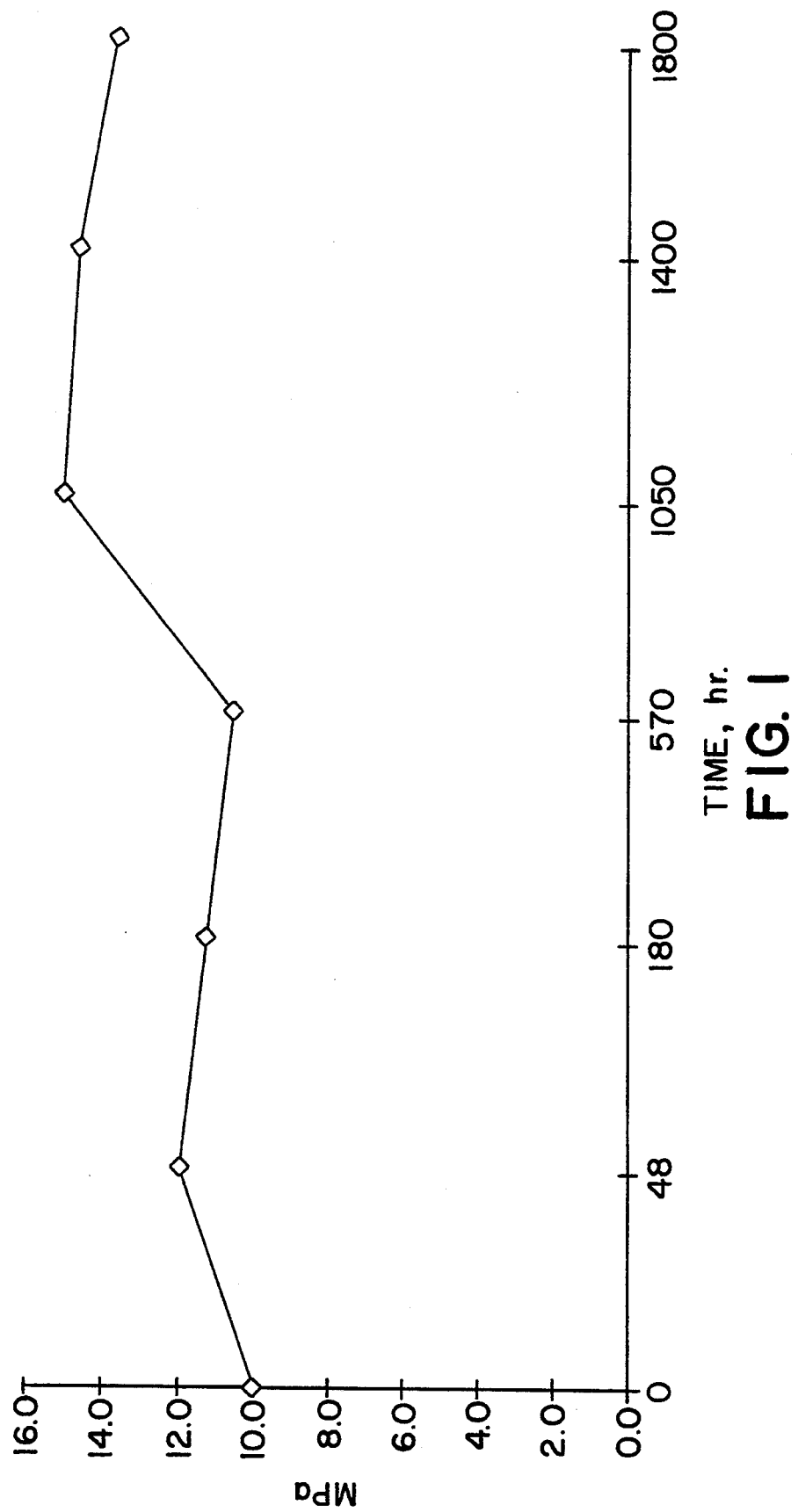
FIG. 1, illustrates the durability of the adhesion of the composition according to the present invention following immersion in water at 37° C. As can be noticed, after immersion in a bath with water for 1050 hours, a strength of 14 MPa was obtained.
Figure 2:
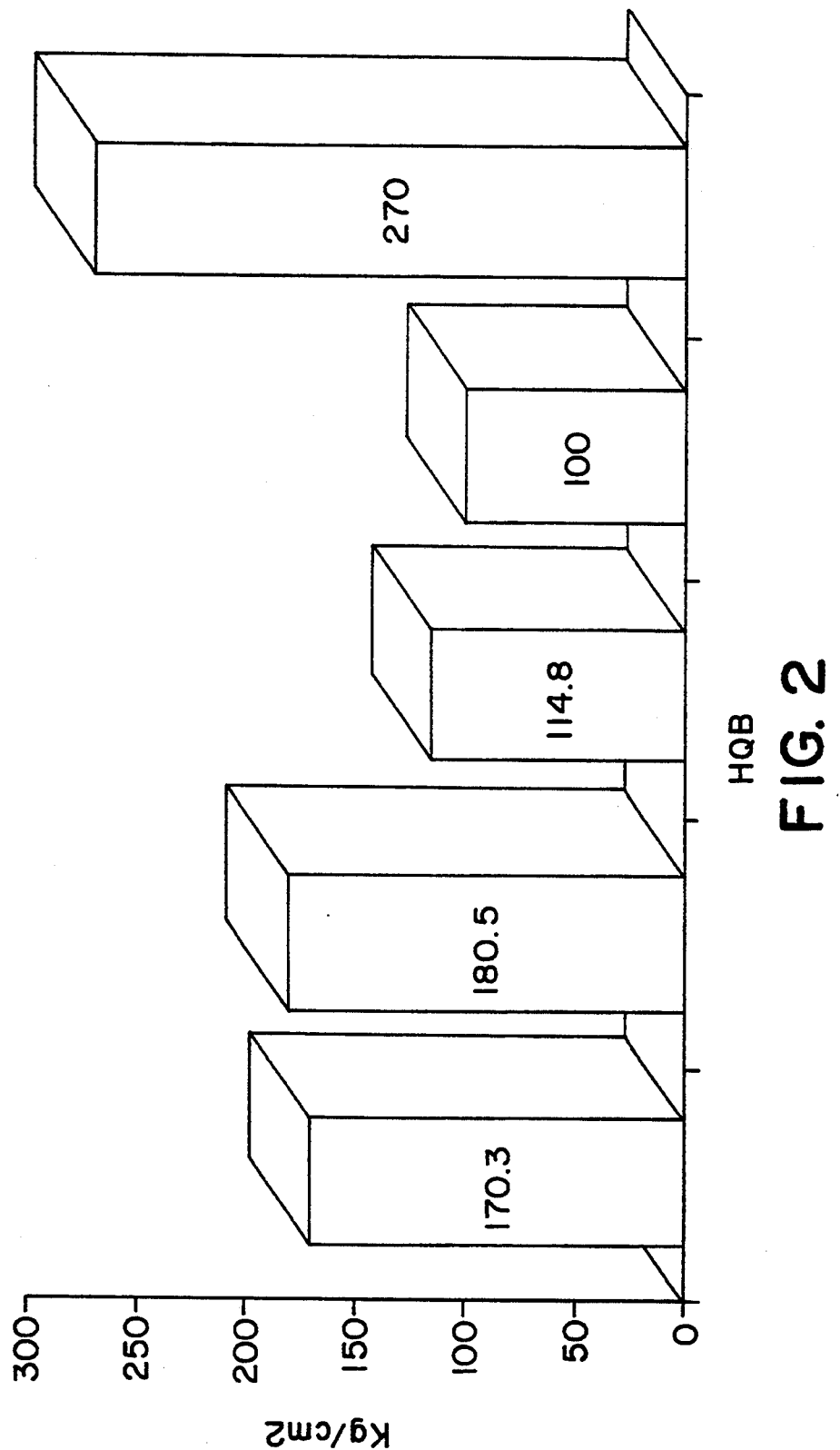
FIG. 2, illustrates the tensile adhesive strength, measured in kg/cm², of the composition according to the present invention (HQB) to Ni-Cr alloy and four commercial adhesive compositions. As can be noticed, the tensile strength of the present composition is superior to that of other known adhesive compositions.
Figure 3:
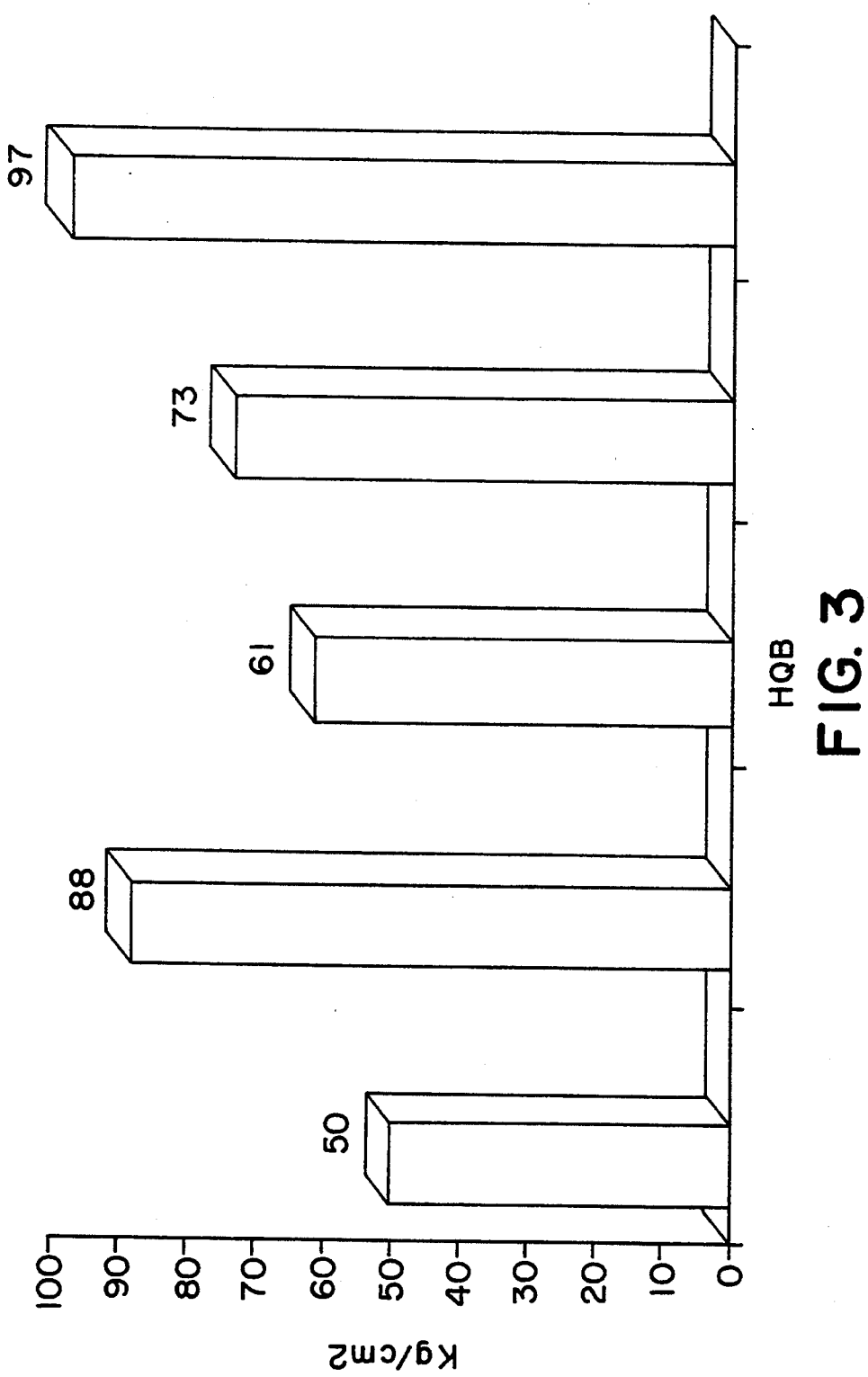
FIG. 3, illustrates the tensile adhesive strength to dentin of the composition according to the present invention, in comparison with some commercial adhesive dental compositions. The strength obtained with the present composition was the highest one.
Figure 4:
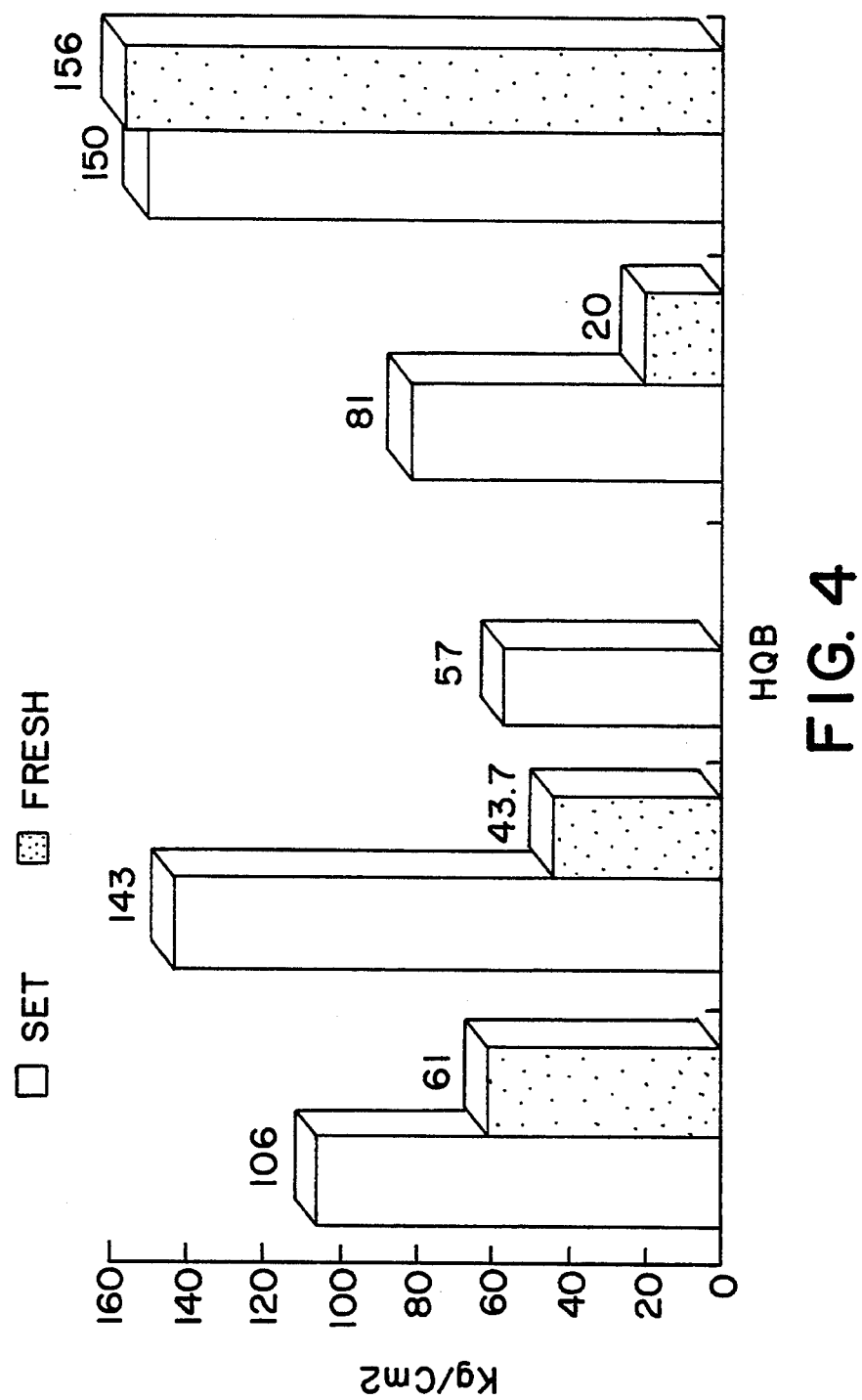
FIG. 4, illustrates the tensile adhesive strength to set and to fresh amalgam using the composition according to the present invention and four commercial adhesive compositions. As can be noticed, the tensile adhesive strength of the present composition, is much superior than that of other known adhesive dental compositions.
Figure 5:
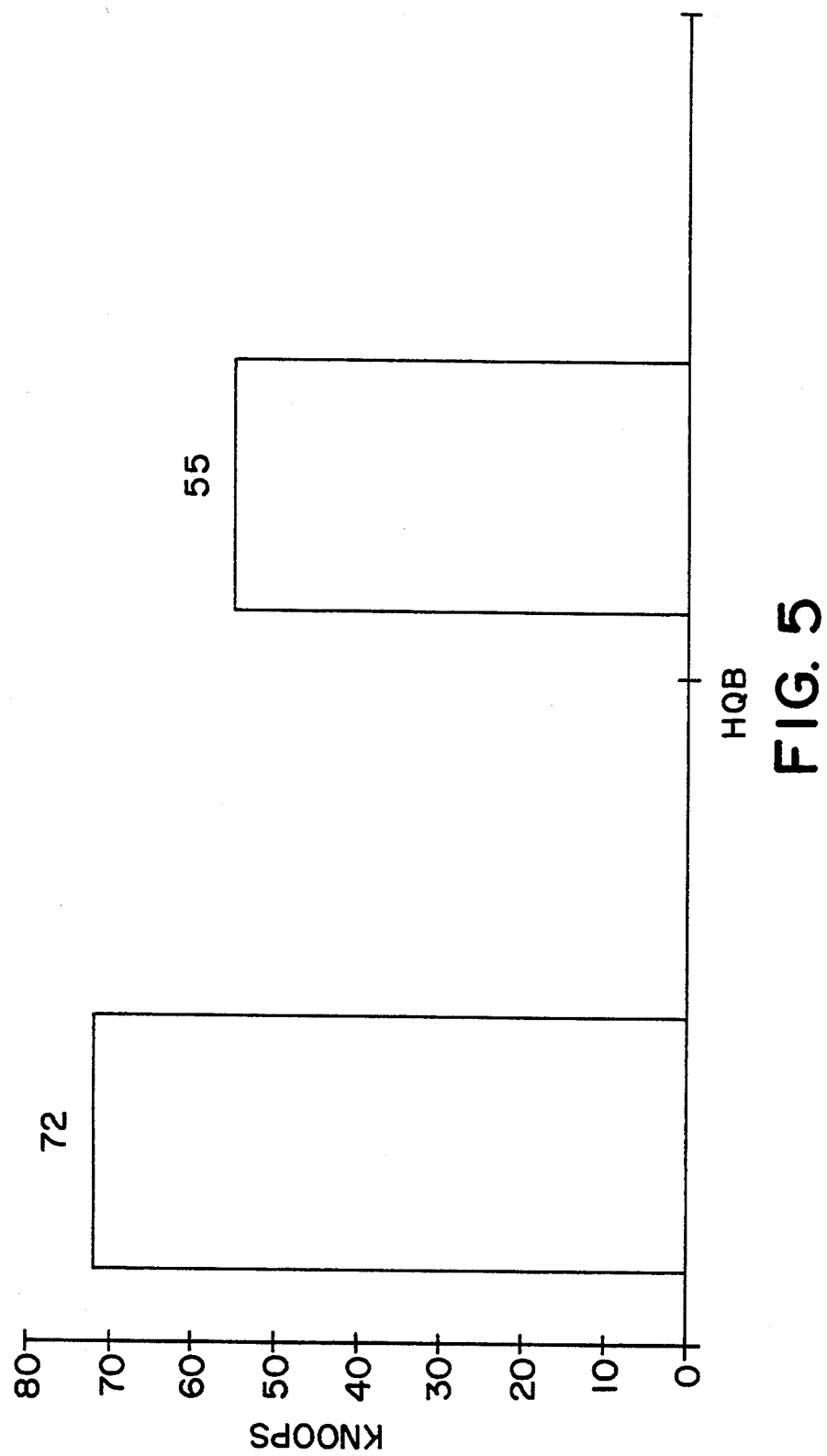
FIG. 5, illustrates the hardness (measured by a Rockwell hardness tester according to ASTM D785-81 of the composition as produced in Example 16) and a commercial composition. The difference of 17 Knoops units is quite significant.

It was found that the compositions according to the present invention has an excellent adhesiveness not only to the tooth tissue—dentine and enamel—but also to the amalgam layer, either fresh or old. Due to its outstanding affinity for the tooth and its ability to penetrate the surface, the composition would provide a bonded structure which is characterized by its outstanding resistance and durability in water (see FIG. 1).

One of the important characteristics of a dentine bonding agent, is its ability to penetrate into the dentinal tubels on a molecular level. When a monomer infiltrates the dentinal tubel and polymerizes in-situ, it creates a resin impregnated layer. This layer resulting from the combination of the resin with dentinal collagen, provides a very strong and stable dentile bond.

In contrast to known adhesive compositions for teeth as described in the prior art, which require a prior treatment with a strong mineral acid in order to impart a high bondability to teeth, these compositions do not require the acid treatment, since the tensile adhesive strength which is obtained by the incorporation of at least one of the above compounds is sufficiently high, surpassing in most of the cases, a value of 110 Kg/cm².

The catalyst to be used in the adhesive compositions is selected from known free-radical catalysts. These catalysts may be of the photopolymerization type or chemical initiators. Typical examples are organic peroxides and azo-compounds, such as benzoyl benzoyl peroxide, azo-bis-isobutyronitrile, etc. The amount of these catalysts is generally in the range of 0.05% to 5.0% by weight of the composition. In case of a photopolymerization catalyst, the composition would contain a, promoter and crosslinking agent as known in the art.

There are cases when it is desirable to incorporate in the polymerization mass an inhibitor, such as hydroquinone in order to have a better control on the extent of polymerization mass, so that the time for the polymerization should be maintained in the range of between 10 to 15 minutes.

Summing up, the adhesive compositions according to the present invention is characterized by the following main advantageous properties:

Impart high bonding values to dentin, enamel, porcelain, set and fresh amalgam.

Possess high durability following exposure to oral environment.

Can be applied as an intermediate bonding layer, or as the filler material itself.

Behave as an inert system, not being sensitive to the surrounding.

While the invention will be hereinafter described by a number of Examples, it should be clearly understood that these Examples are presented only for a better understanding of the invention, without limiting its scope. A person skilled in the art after reading the present specification will be in a position to insert some modifications without being outside the boundaries of the invention as covered by the appended Claims.

In the Examples, the tensile strength was determined by using a machine produced by Zwick Werktoff-Pru Maschinenn in accordance with ASTM-D-87778 (1983).

It should be pointed out that Examples 19, 20, 21 and 22 do not illustrate the present invention and are presented only for comparison purposes.

In the Examples below, the percentages are given by volume, unless otherwise stated.

EXAMPLE 1

The sample tested consisted of a rod, 14 mm diameter, of polymethylmethacrylate (PMMA) having a cavity designed with an undercut, the bottom of which being covered with "fresh" amalgam (immediately after trituration).

A solution of 10% (by weight) of 4-META in acetone was brushed over the cavity. Subsequently a mixture was added consisting of the following ingredients: 0,5 g of 10% solution 4-META in acetone, 2 g methylmethacrylate (MMA),
0,04 g Co-naphthenate,
0,1 g Peroxide of methyl-ethyl ketone,
3 g PMMA (polymethylmethacrylate), and
0,17 g metallic powder (with particle size of about 20µ) consisting of 45% Ag, 30% Sn and 25% Cu (weight percentage).

After 5 minutes, a rod (5 mm diameter) of polymethymethacrylate was placed perpendicular to the curing mass of the sample and left for 24 hours at room temperature.

The sample was then introduced in a container with water and left for 2 hours at 37° C. The rod was then pulled out from the cavity at a loading speed of 5 mm/min using the mechanical Zwick Tester. The adhesive tensile strength was found to be 140 kg/cm$^2$.

EXAMPLE 2

The procedure of Example 1 was repeated, except that on "old" amalgam (24 hr after trituration) was used on the cavity bottom. The adhesive tensile strength, measured as in Example 1, was 140 kg/cm$^2$.

EXAMPLE 3

The procedure of Example 1 was repeated except that the metallic powder used had an average particle diameter of about 7µ. The adhesive tensile strength, measured as in Example 1 was 159 kg/cm$^2$.

EXAMPLE 4

The same procedure as in Example 1 was repeated except that the metallic powder used in the composition was a powder consisting of Ag (72%) and Cu (28%) having an average diameter of the particles of 20 microns.

The adhesive tensile strength, measured as in Example 1, was 120 kg/cm$^2$.

EXAMPLE 5

The same procedure as in Example 1 was repeated except that instead of methylmethacrylate (MMA), the same amount of glycidylmethacrylate (GMA) was added.

The adhesive tensile strength, measured as in Example 1, was 102 kg/cm$^2$.

EXAMPLE 6

The same procedure as in Example 1 was repeated except that to said composition a mixture of ethers of α-cyano-acrylic acid was added.

The adhesive tensile strength, measured as in Example 1, was 110 kg/cm$^2$.

EXAMPLE 7

The procedure as in Example 1 was repeated except that to the composition used therein, it was added an amount of 0.15 g of a material having the following composition (wt. percentage):
SiO$_2$: 30%; CaF$_2$: 35%; Al$_2$O$_3$: 20%;
AlF$_3$: 2.5%; NaF: 2.5%; Al$_3$PO$_4$: 10%;
Samples were kept for 24 hours at room temperature and then introduced in water maintained at 37° C. for about 2 hours. The adhesive tensile strength, measured as in Example 1, was 130 kg/cm$^2$.

EXAMPLE 8

The same sample (polymethylmethacrylate rod, diameter of 14 mm) with a cavity, the bottom of which was covered with fresh amalgam (immediately after trituration) was used.

A solution of 4-META (10% by wt) in acetone was coated onto the fresh amalgam surface using a small brush. Then a mixture was prepared having the following composition: 0.75 g methylmethacrylate monomer; 0.05 g of a metal powder consisting of 45% Ag, 30% Sn and 25% Cu (having an average diameter of 7 u); 0.04 g of 4-META-powder; 0.02 g of partially oxidized tri-n-butylborane as catalyst and 0.7 g of polymethymethacrylate as a filler.

The composition was put in the cavity and a polymethylmethacrylate rod (5 mm diameter) was placed on the curing mass at room temperature for 24 hours.

The samples were introduced in water and maintained at 37° C. for 2 hours. The adhesive tensile strength, measured as in Example 1, was 146 kg/cm$^2$.

EXAMPLE 9

The procedure as in Example 8, was repeated except that the composition was cured on the surface of an "old" amalgam (24 hours after trituration).

The adhesive tensile strength, measured as in Example 1, was 140 kg/cm$^2$.

EXAMPLE 10

The procedure as in Example 9, was repeated except that to the composition used therein it was added a material having the following composition:
4-META powder: 0.04 g
methylmethacrylate: 0.75 g.
polymethylmethacrylate: 0.7 g.
t-n-butyl-borane: 0.12 ml.
SiO$_2$: 0.03 g.
Al$_2$O$_3$: 0.02 g.
AlF$_3$: 0.003 g.
CaF$_2$: 0.031 g.
NaF: 0.0025 g.
AlPO$_4$: 0.01 g, and
a metal powder 0.05 g (having a composition as in Example 8), with a particle size of 7µ.

The adhesive tensile strength, measured as in Example 1, was 115 kg/cm$^2$.

EXAMPLE 11

The procedure as in Example 9, was repeated adding to the composition also an amount of 0.06 g of a commercial cyanoacrylic-based glue (Loctite- Trade Mark). The curing composition was placed on the fresh amalgam surface.

The adhesive tensile strength, measured as in Example 1, was 107 kg/cm$^2$.

EXAMPLE 12

The procedure of Example 11 was repeated except that the curing composition was placed on an old amalgam (24 hours after trituration) surface.

The adhesive tensile strength measured as in Example 1 was 121 kg/cm$^2$.

EXAMPLE 13

The procedure as in Example 9 was repeated, but an amount of 0.08 g of titanium oxide (with an average particles size of about 3µ) was added.

The adhesive tensile strength, measured as in Example 1, was 134 kg/cm$^2$.

EXAMPLE 14

The sample tested consisted of a rod (14 mm diameter) of polymethacrylate having a cavity, the bottom of which being covered with old amalgam.

A solution of 5% 4-META in acetone was brushed over the cavity. Subsequently, a mixture was added having the following composition:

0.08 g of 4-META; 1.4 g of methylmethacrylate; 0.9 g of polymethylmethacrylate and 0.12 g of a metallic powder (45% Ag, 30% Sn and 20% Cu). As catalyst for the reaction, a photosensitizer was used which consisted of 0.13 g of camphorquinone and 0.06 g of triethylamine.

The rod (5 mm diameter) of polymethylacrylate was placed on the curing mass on said sample and irradiated with visible light (Aristocrat VL unit from C. Healthco International) for 60 seconds. The sample was left for two hours at room temperature.

The adhesive tensile strength, measured as in Example 1, was 131 $kg/cm^2$.

EXAMPLE 15

The procedure as in Example 14 was repeated but instead of said metallic powder, an amount of 0.5 g of silica (average particle size of about 10 nm diameter) was added.

The adhesive tensile strength, measured as in Example 1, was 123 $kg/cm^2$.

EXAMPLE 16

An experiment was carried out using a photopolymerization catalyst for the composition.

The sample tested consisted of two rods: one of 5 mm diameter of polymethylmethacrylate (PMMA) and one of Cermalloy (alloy of Cr-Ni), which is often used in the restoration practice of teeth. A solution of 5% of 4-META was brushed over the rod's surfaces and after drying, a mixture was added consisting of the following two parts:

| (a) Dry part: | |
|---|---|
| Polymethylmethacrylate | 0.96 g; |
| Silica | 0.83 g; |
| A metallic powder consisting of 72% Ag and 28% Cu, having a particle size of 20μ | 0.02 g; |
| 4-META | 0.08 g; |
| b) Liquid part: | |
| Methylmethacrylate | 1.00 g; |
| Chloropropoxythioxanthone-photoinitiator | 0.016 g; |
| Ethyl-4-dimethylaminobenzoate-promoter | 0.02 g; |
| Camphorquinone | 0.023 g; |
| Uvercryl (Trade Mark of Sartomer Company) used as initiator | 0.1 g and |
| Trimethylol-propanetriacrylate, used as crosslinking | 0.47 g |

The curing mass was placed between two rods which were irradiated with visible light for 40 seconds till full curing. The samples were left for two hours at room temperature and for 500 hours were kept in water at 37° C. The adhesive tensile strength, measured as in Example 1, was as follows:

For perspex-perspex 187 $kg/cm^2$;
For perspex-Cermalloy 220 $kg/cm^2$.

EXAMPLE 17

An experiment was carried out a using chemical initiator as catalyst. The procedure as in Example 16, was used, but the liquid part (b) consists of:

| | |
|---|---|
| Methylmethacrylate | 1.0 g; |
| Dimethyl-p-toluidine | 0.007 g; and |
| Benzoylperoxide | 0.009 g. |

The adhesive tensile strength measured as in Example 16 was 200 $kg/cm^2$ Perspex-Perspex.

As would be noticed from the comparative Example 22, the polymerization with the same chemical initiators but with dry metal salts instead of metallic powder, failed to impart a solid mass.

EXAMPLE 18

The procedure as in Example 17 was repeated, but in the dry part (a) an amount of 0.02 g of titanium dioxide was added, in order to achieve a light colour of the curing mass.

The adhesive tensile strength, measured as in Example 17 was 192 $kg/cm^2$ perspex-perspex.

EXAMPLE 19 (comparative)

The procedure as in Example 1 was repeated, but no metalic powder was added in the composition.

The adhesive tensile strength, measured as in Example 1, was only 30 $kg/cm^2$.

EXAMPLE 20 (comparative)

The procedure as in Example 16 was used (without any metallic constituent) but a solution of 4 molar tetrahydrofuran was used as a primer and the amalgam was "old" (24 hours after trituration) containing 20% by weight of polymethylmethacrylate powder.

The adhesive tensile strength, measured as in Example 1, was 33.6 $kg/cm^2$.

EXAMPLE 21 (comparative)

The procedure as in Example 16 was repeated, but instead of using the metallic powder of Ag-Cu, the respective metal salts of two cations mentioned in the W 85/00514 patent application, i.e. iron oxalate and copper nitrate, were used in an amount equivalent to the metallic powder incorporated in the Example 16.

The dry part consisted of the following constituents:

| | |
|---|---|
| polymethylmethacrylate | 0.96 g |
| Silica | 0.8 g |
| 4-META | 0.08 g |
| copper nitrate | 0.02 g |
| iron oxalate | 0.05 g |

The liquid part was the same as in the Example 16 using the same amounts of the reagents.

The adhesive tensile strength was measured for the same systems as in Example 16, and the following results were obtained:

| | |
|---|---|
| perspex-perspex: | 120 $kg/cm^2$ |
| perspex-fresh amalgam | 25 $kg/cm^2$ |
| perspex-old amalgam | 60 $kg/cm^2$ |

| -continued | |
|---|---|
| perspex-Cermalloy | 100 kg/cm² |

EXAMPLE 22 (comparative)

The experiment as in Example 17 was repeated, using the same chemical initiators but with the composition of the dry part containing the metal salts as used in the above Example 21.

The composition did not cure even after 24 hours, so that tensile strength could not be measured.

We claim:

1. A dental composition useful as adhesive and for the restoration of teeth which comprises a polymer produced from a methacryloxyethyl trimellitic acid anhydride (4-META) and methyl methacrylate monomer in the presence of a catalyst, and optionally an inhibitor, said dental composition characterized in that said polymer has incorporated therein at least one metallic compound selected from the group consisting of: tin, silver, copper and nickel, in an amount between 1% and 50% by volume of the polymer composition, said dental composition optionally also including a material capable of releasing fluoride anions.

2. The dental composition according to claim 1, wherein two of said metallic compounds are incorporated.

3. The dental composition according to claim 2, wherein the amount of the metallic compounds incorporated is between 2% and 20% by volume of said polymer composition.

4. The dental composition according to claim 1, wherein the particle size of the metallic compound incorporated is in the range of 5 to 50 microns.

5. The dental composition according to claim 1, wherein said fluoride-based material is added in an amount of between 1 and 10% by weight of said polymeric composition.

6. The dental composition according to claim 1, wherein in said catalyst is a free-radical catalyst.

7. The dental composition according to claim 6, wherein said free-radical catalyst is selected from a chemical initiator and a photosensitizer.

8. The dental composition according to claim 6, wherein the amount of the free-radical catalyst is in the range of between 0.05% to 5% by weight of said polymeric composition.

9. The dental composition according to claim 7, wherein said photosensitizer comprises camphorquinone and triethylamine.

* * * * *